United States Patent [19]

Grunwald

[11] Patent Number: 4,925,630

[45] Date of Patent: May 15, 1990

[54] SAMPLE VIALS TRAY

[76] Inventor: James L. Grunwald, 520 Young Dr., Owatonna, Minn. 55060

[21] Appl. No.: 352,725

[22] Filed: May 16, 1989

[51] Int. Cl.[5] .......... C12M 1/00

[52] U.S. Cl. .......... 422/104; 422/65; 422/297; 422/300; 435/287; 211/74

[58] Field of Search .......... 422/104, 65, 297, 300; 435/287; 211/74

[56] References Cited

U.S. PATENT DOCUMENTS

| | | | |
|---|---|---|---|
| 3,682,597 | 8/1972 | Husch | 422/104 X |
| 3,802,844 | 4/1974 | Sendra et al. | 211/74 X |
| 4,389,374 | 6/1983 | Sutton et al. | 422/104 |
| 4,407,958 | 10/1983 | DeGratt, Jr. | 435/287 |
| 4,495,150 | 1/1985 | Cook et al. | 211/74 X |
| 4,534,465 | 8/1985 | Rothermel et al. | 211/74 X |
| 4,748,125 | 5/1988 | Pizzolante | 435/287 |

*Primary Examiner*—Barry S. Richman
*Assistant Examiner*—Lynn M. Kummert
*Attorney, Agent, or Firm*—George R. Nimmer

[57] ABSTRACT

For vial samples of milk collected along a route of dairy farms, a sample vials tray is provided of foldable mode that can be readily accommodated within the limited-volume ice chest of the route agent's truck. At the agent's milk processing plant, the same tray, and with the sample vials undisturbed therein, can be employed in the non-folded and latched condition required for automated laboratory analysis of milk samples contained in the tray-housed vials. A multi-prongs type holder holds each vial in a secure condition during the vehicular journey from dairy farm to milk processing plant. The foldable tray utilizes a special hinge that is relegated to a non-obtrusive location that does not interfere with the tray's usage in concert with automated laboratory analytical equipment.

10 Claims, 2 Drawing Sheets

SAMPLE VIALS TRAY

BACKGROUND OF THE INVENTION

Milk collected from dairy animals is charged by the dairy farmer into farmstead refrigerated tanks to await a trucker agent from a milk processing plant. During his/her farmstead visit, the trucker agent determines whether the milk sanitation merits being pumped into the truck tank for delivery to the processing plant. Assuming the milk is sanitary and merits being pumped into the truck tank, the agent samples the dairy farm's milk into a cylindrical vial which is identified and placed into a rectangular rack located within a truck ice chest. At the processing plant laboratory, the farm's vial sample is qualitatively evaluated. In fact, with automated laboratory analytical equipment, vial samples from numerous dairy farms can be placed into a multi-compartments and ratchetably-conveyable lineal tray cartridge for the automatic laboratory equipment.

The aforementioned milk collection, vial sampling, and automated qualitative analysis procedure would be more sanitary and efficient if the multi-compartments and ratchetably-conveyable laboratory trays were employed at the dairy farm by the trucker agent whereby milk sample vials might be handled but once prior to laboratory qualitative analysis. However, though currently available laboratory trays are desireably lengthy for automated analysis, they are too lengthy for storage within the pickup agent's truck ice chest. Moreover, currently available laboratory trays do not hold vial samples sufficiently securely for traversal along unpaved rural roadways.

OBJECTIVE OF THE INVENTION

In view of the foregoing, it is the general objective of the present invention to provide a multi-compartments and ratchetably-conveyable lineal sample vials tray having a length sufficient for enabling rapid qualitative analysis of numerous vial samples but which lineal tray can be accommodated within limited-volume truck ice chest, and can securely hold vial milk samples ancillary rural roadway travel, and with the net result that individual vial samples need be handled but once between milk farm collection and automated laboratory analysis.

GENERAL STATEMENT OF THE INVENTION

With the above general objective in view, and together with other ancillary and specific objectives which will become more apparent as this description proceeds, the sample vials tray of the present invention generally comprises a pair of substantially equallength C-shaped channel members wherein the horizontal upper-leg is multi-apertured to accommodate the upper portion of a sample vial and wherein the horizontal lower-leg (and in alignment with upper-leg apertures) is provided with integral holders for engaging the lower portion of a sample vial, said channel members vertical central-leg being provided with ratchetable openings, and said channel members being pivotably attached and into latchable linearity with a nonobtrusive hinge means that does not interfere with the tray's usage in concert with automated laboratory analytical equipment.

GENERAL DESCRIPTION OF THE DRAWING

In the drawing, wherein like characters refer to like parts in the several views, and in which.

DETAILED DESCRIPTION OF THE DRAWING

Figure 1:
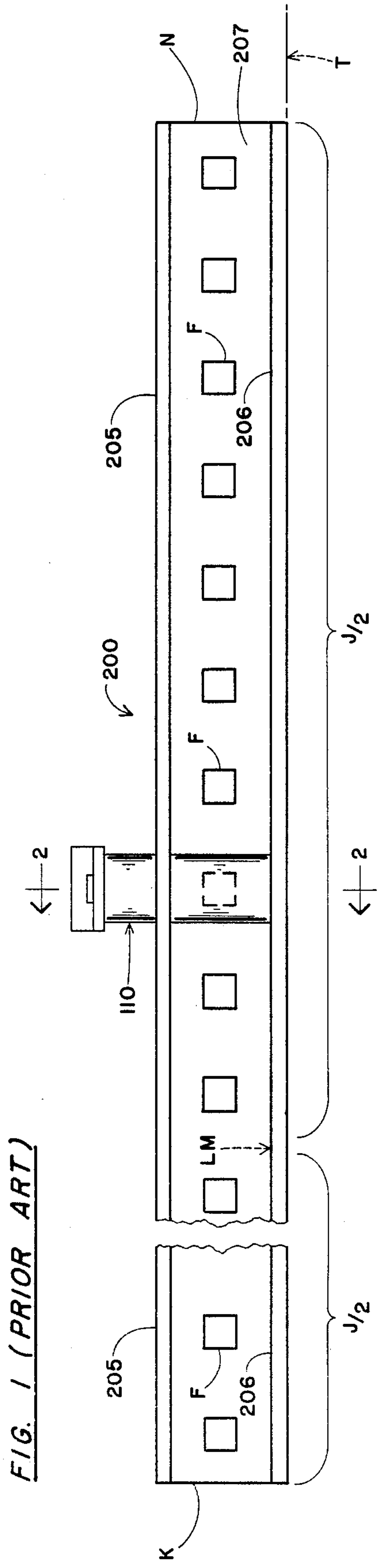
FIG. 1 (PRIOR ART)
FIG. 1 is a side elevational view of a sample vials tray of the prior art.
Figure 2:
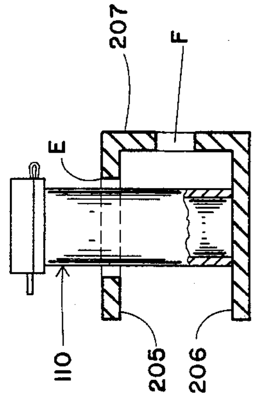
FIG. 2 (PRIOR ART)
FIG. 2 is a sectional elevational view taken along line 2—2 of FIG. 1.

Turning initially to drawing FIGS. 1 and 2 which depict a prior art sample vials tray consisting of a channel member 200 that extends for a finite-length "J" between a lead-end "K" and a trail-end "N". "LM" indicates a channel midpoint spaced a length "J"/2 from end "K" and also from end "N". Channel horizontal roof-panel 205, horizontal floor-panel 206, and upright side-panel 207, each extending rigidly and uninterruptedly at finite-lengths "J" between channel ends "K" and "N". Roof-panel 205 is provided with circular apertures "E" to surround the upper portion of sample vials 110. The vial lower end rests upon and is laterally unsecured at the planar upper-surface of floor-panel 206. Side-panel 207 is provided with a plurality of ratchetable-openings "F" therealong for automated laboratory analysis and during which channel 200 moves along laboratory table "T". For the purposes of efficient laboratoring processing, finite-length "J" should be sufficiently lengthy to accommodate about twenty sample vials (110) and, of course, an equal number of roof-panel apertures ("E").

Turning now to drawing FIGS. 3–6 which depict a representative embodiment 9 of the sample vials tray of the present invention. Embodiment 9 comprises a pair of similar channels (100A, 100B), each of which is similar to prior art channel 200 in that there is a horizontal and multi-apertured ("E") roof-panel (105A, 105B) overlying a horizontal floor-panel (106A, 106B) and an upright side-panel (107A, 107B) provided with ratchetable-openings ("F").

However, differing from prior art channel 200, each of the embodiment 9 channels (100A, 100B) has an arrested length ("J"/2) that is substantially one-half finite-length "J" of prior art channel 200. Specifically, first-channel 100A extends for a distance "J"/2 from tray trail-end "K" to midpoint "LM", and second-channel 100B extends for a distance "J"/2 from tray lead-end "N" to midpoint "LM". Also differing from prior art channel 200, the embodiment 9 floor-panels (106A, 106B) are provided with upstanding springy prongs ("P") and vertically arrayed in alignment with each roof-panel aperture ("E") to removably engage and laterally restrain the lower portion of a sample vial (110). Such prongs "P" may be struck from the floor-panel structural material.

Figure 3:
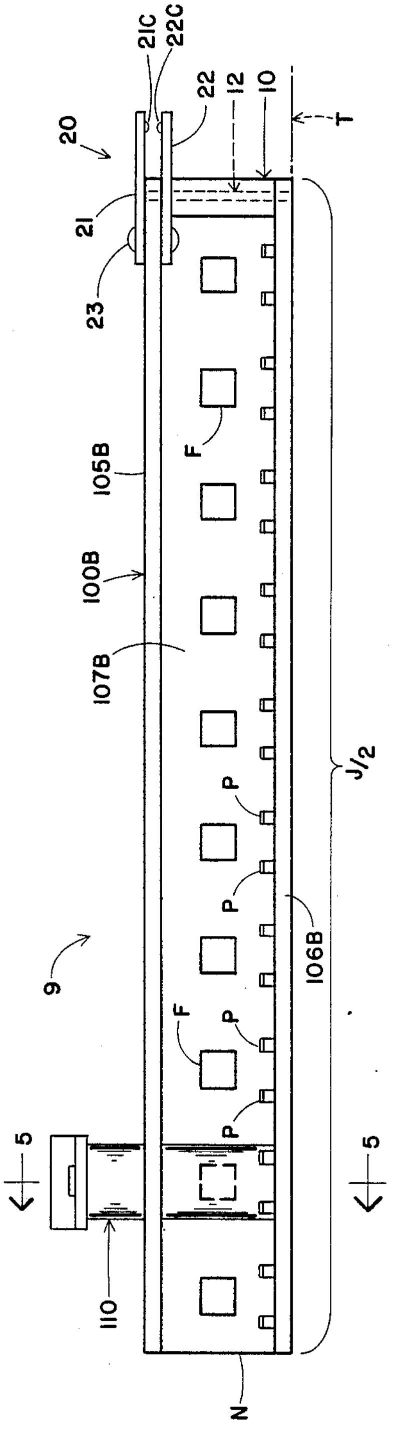
FIG. 3 is a side elevational view of a representative embodiment ("9") of a sample vials tray of the present invention and in a vials storage mode.
Figure 4:
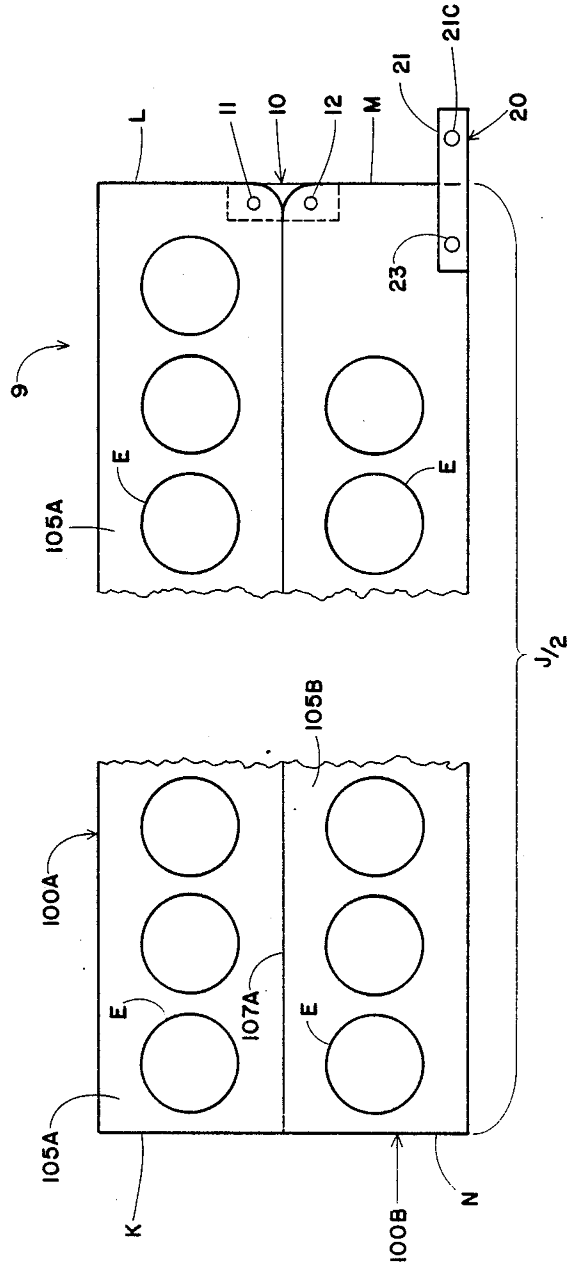
FIG. 4 is a top plan view of representative embodiment "9" in the vials storage mode.
Figure 5:
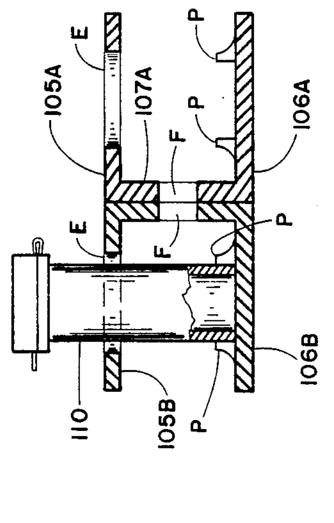
FIG. 5 is a sectional elevational view taken along line 5—5 of FIG. 3.

At the sample vials tray midpoint ("L", "M"), hinge means (e.g. 10–12) pivotably connect first-channel 100A to second-channel 100B whereby said tray (e.g. 9) can be alternatively employed:

(i) as suggested in FIGS. 3–5: in a stored vials, folded mode wherein the exposed outer-surface of the first-channel sidepanel (107A) lies alongside the exposed outer-surface of the second-channel side-panel (107B). The overall length "J"/2 for the folded mode enables tray 9 to be easily accommodated within the limited-volume ice chests of collector agents' trucks, and (ii) as suggested in FIG. 6: in a vials laboratory analysis mode wherein the side-panels (107A, 107B) extending colinearly in opposite directions from the tray midpoint ("L", "M"). Located remote fromthe hinge means and attached to one channel (e.g. 100B), a releasable latch means (e.g. 20) maintains the upright outer-surfaces of side-panels 107A and 107B in a coplanar relationship appropriate to automated laboratory analysis.

Figure 6:
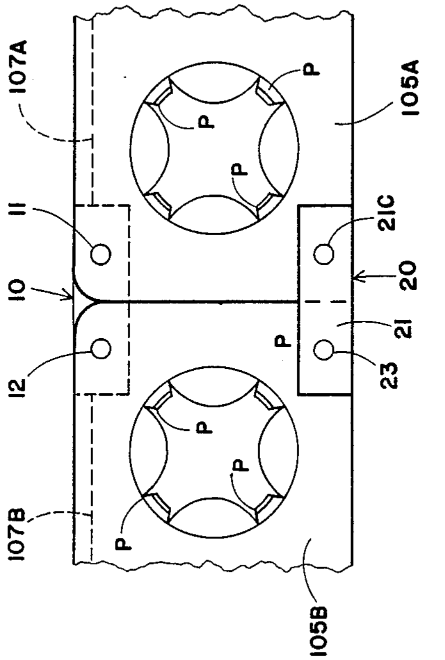
FIG. 6 is a detail top plan view of representative embodiment "9" in the laboratory analysis mode.

Appropriate to the laboratory analysis mode, the hinge means is relegated inwardly from the side-panels outer-surfaces. The hinge means depicted comprises an upright bar 10 that is connected with first-pin means (11) to the roof-panel and floor-panel of first-channel 100A and with second-pin means (12) to the roof-panel and floor-panel of second-channel 100B. As indicated in FIG. 6, a finite gap exists between colineal side-panels 107A and 107B, and which gap is bridged by the horizontally extending width of upright bar 10.

A preferred latch means comprises a pair of springy plates including an upper-plate 21 and a lower-plate 22 attached to opposite surfaces of second-channel roof panel 105B, such as with rivet 23. Beyond tray midpoint "M", upper-plate 21 is provided with a downward boss 21C and lower-plate 22 is provided with an upward boss 22C and thereby enhance removable engagement with first-channel 100A (at "L").

From the foregoing, the construction and operation of the sample vials tray will be readily understood and further explanation is believed to be unnecessary. However, since numerous modifications and changes will readily occur to those skilled in the art, it is not desired to limit the invention to the exact construction shown and described, and accordingly, all suitable modifications and changes may be resorted to, falling within the scope of the appended claims.

I claim:

1. Sample vials tray having a finite-length extending between a lead-end and a trail-end, said tray having a midpoint located substantially midway said lead-end and trail-end and comprising:

(A) a first-channel extending lengthwise from said trail-end to said midpoint and comprising:

(Ai) a horizontal roof-panel having means defining a plurality of apertures spaced therealong to accommodate an upper portion of each of a plurality of sample vials, (Aii) a horizontal floor-panel, and (Aiii) an upright side-panel connection between said first-channel roof-panel and said floor-panel, said side-panel having a pair of upright planar opposed surfaces including an inner-surface and an outer-surface;

(B) a second-channel extending lengthwise from said lead-end to said midpoint and comprising:

(Bi) a horizontal roof-panel having means defining a plurality of apertures spaced therealong to accommodate an upper portion of each of a plurality of sample vials, (Bii) a horizontal floor-panel, and (Biii) an upright side-panel connection between said second-channel roof-panel and said floor-panel, said side-panel having a pair of upright planar opposed surfaces including an inner-surface and an outer-surface;

(C) at said tray midpoint, hinge means pivotably connecting said first-channel to said second-channel, said hinge means being located at the side-panels of both channels but being relegated inwardly from outer-surfaces of said side-panels whereby said tray can be alternatively employed:

(Ci) a stored vials, folded mode wherein the outer-surface of the first-channel side-panel lies alongside the outer-surface of the second-channel side-panel, and (Cii) a vials laboratory analysis mode wherein the side-panels of the two channels extend colinearly in opposite directions from the tray midpoint; and (D) located wholly remote from said hinge means, latch means attached to one channel to releasably latch the other channel into colinearity with the one channel and thereby releasably maintain the laboratory analysis mode for said sample vials tray.

2. The sample vials tray of claim 1 wherein the side-panels of both channels have means defining ratchetable-openings spaced therealong and for usage during said laboratory analysis mode.

3. The sample vials tray of claim 1 wherein the first and second channels floor-panels are provided with an array of upstanding springy prongs to removably engage a lower portion of a sample vial, each in vertical alignment with a respective roof-panel aperture.

4. The sample vials tray of claim 3 wherein the latch means comprises a pair of springy plates including an upper-plate and a lower-plate attached to opposite sides of the second-channel roof-panel and extending beyond said second-channel toward the roof-panel of the first-channel.

5. The sample vials tray of claim 4 wherein the side-panels of both channels have means defining ratchetable-openings spaced therealong and for usage during said laboratory analysis mode.

6. The sample vials tray of claim 1 wherein the hinge means comprises an upright bar that is pivotably connected with first-pin means to the roof-panel and floor-panel of the first-channel and that is also pivotably connected with second-pin means to the roof-panel and floor-panel of the second-channel.

7. The sample vials tray of claim 6 wherein for the laboratory analysis mode a finite gap exists between the colineal side-panels and wherein said upright bar bridges said finite gap.

8. The sample vials tray of claim 7 wherein the latch means comprises a pair of plates including an upper-plate and a lower-plate attached to opposite sides of the second-channel roof-panel and extending beyond said second-channel toward the roof-panel of the first-channel.

9. The sample vials tray of claim 8 wherein the first and second channels floor-panels are provided with an array of upstanding springy prongs to removably engage a lower portion of a sample vial, each in vertical alignment with a respective roof-panel aperture.

10. The sample vials tray of claim 9 wherein the side-panels of both channels have ratchetable-openings spaced therealong and for usage during said laboratory analysis mode.

* * * * *